(12) United States Patent
Hansen et al.

(10) Patent No.: US 10,842,588 B2
(45) Date of Patent: Nov. 24, 2020

(54) SURGICAL INSTRUMENT ASSEMBLY

(71) Applicant: 3DINTEGRATED APS, Copenhagen N (DK)

(72) Inventors: Steen Moller Hansen, Skodstrup (DK); Henriette Schultz Kirkegaard, Copenhagen V (DK); Andre Hansen, Copenhagen N (DK)

(73) Assignee: 3DINTEGRATED APS, Copenhagen (DK)

( * ) Notice: Subject to any disclaimer, the term of this patent is extended or adjusted under 35 U.S.C. 154(b) by 31 days.

(21) Appl. No.: 16/066,417

(22) PCT Filed: Dec. 29, 2016

(86) PCT No.: PCT/DK2016/050475
§ 371 (c)(1),
(2) Date: Jun. 27, 2018

(87) PCT Pub. No.: WO2017/114538
PCT Pub. Date: Jul. 6, 2017

(65) Prior Publication Data
US 2019/0008603 A1    Jan. 10, 2019

(30) Foreign Application Priority Data
Dec. 30, 2015 (DK) .................. 2015 70890

(51) Int. Cl.
*A61B 90/30* (2016.01)
*A61B 1/06* (2006.01)
(Continued)

(52) U.S. Cl.
CPC ............... *A61B 90/30* (2016.02); *A61B 1/06* (2013.01); *A61B 1/32* (2013.01); *A61B 17/0469* (2013.01);
(Continued)

(58) Field of Classification Search
CPC ......... A61B 90/30; A61B 90/70; A61B 34/20; A61B 34/30; A61B 17/0469;
(Continued)

(56) References Cited

U.S. PATENT DOCUMENTS 5,697,939 A * 12/1997 Kubota ............... A61B 90/50
606/130
5,762,613 A *  6/1998 Sutton ................. A61B 10/06
600/564

(Continued)

FOREIGN PATENT DOCUMENTS

EP    1870034 A1   12/2007
EP    1967129 A1    9/2008
(Continued)

OTHER PUBLICATIONS

Danish Search Report for Application No. PA 2015 70890, dated Jun. 29, 2016.
(Continued)

*Primary Examiner* — Tessa M Matthews

(57) ABSTRACT

The invention comprises a surgical instrument assembly for minimally invasive surgery. The surgical instrument assembly comprises a light emitting arrangement and a surgical instrument. The surgical instrument has a distal end and a proximal end and comprises a handle portion at its proximal end and a grasper at its distal end, the grasper comprising at least two jaws and having a closed grasper position and an open position where a grasping space is formed between the jaws. The light emitting arrangement comprises a light source for generating light and a projector for projecting at least a beam of light comprising a string shape perpendicular to the optical axis of the beam of light. At least the projector of the light emitting arrangement is at least temporally fixed to the surgical instrument proximally to the jaws and is
(Continued)

arranged to project the string shaped beam of light such that it will be broken upon a lateral movement of an object into the grasping space.

18 Claims, 14 Drawing Sheets

(51) Int. Cl.
    *A61B 17/29*     (2006.01)
    *A61B 90/00*     (2016.01)
    *A61B 17/00*     (2006.01)
    *A61B 34/30*     (2016.01)
    *A61B 17/04*     (2006.01)
    *A61B 17/062*    (2006.01)
    *A61B 1/32*     (2006.01)
    *A61B 34/20*     (2016.01)
    *A61B 90/70*     (2016.01)

(52) U.S. Cl.
    CPC ........ *A61B 17/0483* (2013.01); *A61B 17/062* (2013.01); *A61B 17/29* (2013.01); *A61B 34/20* (2016.02); *A61B 34/30* (2016.02); *A61B 17/0467* (2013.01); *A61B 90/70* (2016.02); *A61B 2017/00407* (2013.01); *A61B 2017/0474* (2013.01); *A61B 2034/2065* (2016.02); *A61B 2090/061* (2016.02); *A61B 2090/0807* (2016.02); *A61B 2090/306* (2016.02); *A61B 2090/3937* (2016.02)

(58) Field of Classification Search
    CPC .............. A61B 17/062; A61B 17/0467; A61B 2034/2065; A61B 2090/306; A61B 1/06; A61B 1/0607; A61B 1/0661; A61B 1/0669; A61B 1/0676
See application file for complete search history.

(56) References Cited

U.S. PATENT DOCUMENTS

| | | | |
|---|---|---|---|
| 2007/0299468 A1* | 12/2007 | Viola ................... | A61B 5/0084 606/205 |
| 2013/0079598 A1* | 3/2013 | Auld ..................... | A61B 3/0008 600/249 |
| 2013/0296712 A1 | 11/2013 | Durvasula | |
| 2014/0236194 A1* | 8/2014 | Deutsch ............... | A61B 17/062 606/148 |
| 2015/0351776 A1* | 12/2015 | Swayze ............ | A61B 17/12177 600/104 |
| 2017/0055819 A1* | 3/2017 | Hansen .................. | A61B 1/06 |
| 2017/0238962 A1 | 8/2017 | Hansen et al. | |
| 2017/0251900 A1 | 9/2017 | Hansen et al. | |
| 2018/0014851 A1 | 1/2018 | Hansen et al. | |
| 2018/0071030 A1* | 3/2018 | Wood ..................... | A61B 90/57 |
| 2019/0025492 A1* | 1/2019 | Bhagavatula ............ | A61B 1/07 |

FOREIGN PATENT DOCUMENTS

| | | |
|---|---|---|
| EP | 2689723 A2 | 1/2014 |
| WO | 2013/163391 A1 | 10/2013 |
| WO | 2014/145110 A1 | 9/2014 |
| WO | 2015/116951 A2 | 8/2015 |
| WO | 2015/124159 A1 | 8/2015 |

OTHER PUBLICATIONS

International Search Report for International Application No. PCT/DK2016/050475, dated Mar. 1, 2017.

DK Patent Application No. PA 2015 70642; entitled "A Depiction System", filed Oct. 9, 2015.

DK Patent Application No. PA 2015 70483 entitled "A Cannula Assembly Kit", filed Jul. 21, 2015.

\* cited by examiner

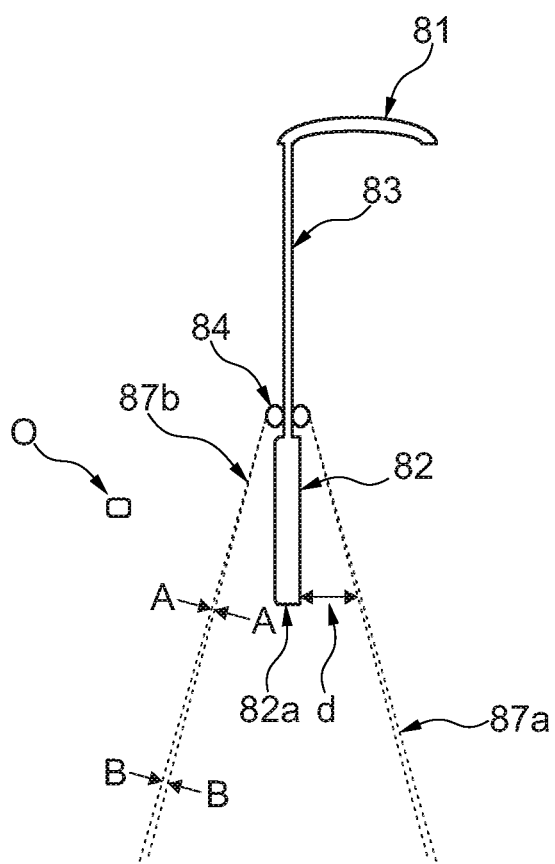
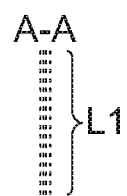
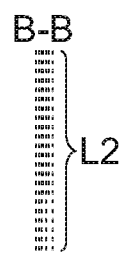
Fig. 13a  Fig. 13b
Fig. 13

SURGICAL INSTRUMENT ASSEMBLY

TECHNICAL FIELD

The invention relates to a surgical instrument assembly for use in minimally invasive surgery. The invention also comprises a sleeve assembly suitable for a surgical instrument assembly, a robot for performing a minimally invasive surgery and a method of performing minimally invasive surgery.

BACKGROUND ART

Minimally invasive surgery has been used increasingly in recent years due to the benefits compared to conventional open surgery as it reduces the trauma to the patient tissue, leaves smaller scars, minimizes post-surgical pain and enables a faster recovery of the patient.

For example, in laparoscopic surgery which is a typical form of minimally invasive surgery the surgeon accesses a body cavity, such as the abdominal or pelvic cavity, through a series of small incisions. A laparoscope is inserted through an incision and conventionally connected to a monitor, thereby enabling the surgeon to see the inside of the abdominal or pelvic cavity. In order to perform the surgical procedure, surgical instruments are inserted through other incisions. In addition, the body cavity around the surgical site is inflated with a fluid, preferably gas e.g. carbon dioxide in order to create an 'air' space within the cavity to make space for the surgeon to view the surgical site and move the laparoscopic instruments.

Invasive surgeries are generally performed through rather small openings in a patient's skin and the surgical site is visualized for the surgeon by inserting a light sensor system e.g. a camera into the body cavity and displaying the images on a screen and/or transmitting the sensed data to a robot surgeon.

In order to improve the surgeon's vision, in particular to make it easier for the surgeon to determine the sizes of various organs, tissues, and other structures in a surgical site, several in-situ surgical metrology methods have been provided in the prior art. Different types of optical systems have been applied to provide an improved vision of the surgical site, which is approaching a 3D vision.

US 2013/0296712 describes an apparatus for determining endoscopic dimensional measurements, including a light source for projecting light patterns on a surgical site including shapes with actual dimensional measurements and fiducials, and means for analyzing the projecting light patterns on the surgical site by comparing the actual dimensional measurements of the projected light patterns to the surgical site.

WO 2013/163391 describes at system for generating an image, which the surgeon can use for measuring the size of or distance between structures in the surgical field by using an invisible light for marking a pattern to the surgical field.

The system comprises a first camera; a second camera; a light source producing light at a frequency invisible to the human eye; a dispersion unit projecting a predetermined pattern of light from the invisible light source; an instrument projecting the predetermined pattern of invisible light onto a target area; a band pass filter directing visible light to the first camera and the predetermined pattern of invisible light to the second camera; wherein the second camera images the target area and predetermined pattern of invisible light, and computes a three-dimensional image.

The above systems highly improve the surgeon's vision for handling the surgical instrument, however, where the surgical instrument comprises a grasper it is still difficult for the surgeon to accurately arrange the surgical instrument and to ensure a correct position prior to grasping, which therefore often leads to erroneous closing of jaws of the grasper which both increases the surgery time and in worst case may lead to tissue damage.

A particular difficulty has been found to be connected to suturing comprising manipulating of a suture needle between two graspers.

DISCLOSURE OF INVENTION

The object of the present invention is to provide a solution for providing good control of the maneuvering of graspers during minimally invasive surgery.

In an embodiment the objective of the invention is to provide a surgical instrument assembly comprising a grasper which can be maneuvered with a relatively high accuracy to ensure a correct position prior to grasping.

In an embodiment the objective of the invention is to provide a surgical instrument assembly comprising a grasper with an improved maneuverability to ensure a correct position prior to grasping, and preferably where the surgical instrument is a needle holder with a reduced risk of slipping or dropping the needle.

In an embodiment the objective of the invention is to provide a robot for maneuvering such a surgical instrument with a relatively high accuracy to ensure a correct position prior to grasping.

These and other objects have been solved by the invention or embodiments thereof as defined in the claims and as described herein below.

It has been found that the invention or embodiments thereof have a number of additional advantages, which will be clear to the skilled person from the following description.

The surgical instrument assembly of the invention comprises a light emitting arrangement and a surgical instrument comprising a grasper with two or more jaws.

According to the invention it has been found that the light emitting arrangement can be applied to increase accuracy of maneuvering the surgical instrument when it is fixed to the surgical instrument to form the surgical instrument assembly as described herein.

The surgical instrument has a distal end and a proximal end and comprises a handle portion at its proximal end and the grasper at its distal end. The grasper has a closed grasper position and an open position where a grasping space is formed between the jaws. The grasping space is the space in which an object such as for example a needle will be grasped upon closing of the jaws.

The light emitting arrangement comprises a light source for generating light and a projector for projecting at least a beam of light comprising a string shape perpendicular to the optical axis of the beam of light. Such a beam of light comprising a string shape perpendicular to the optical axis of the beam of light is herein referred to as a string shaped beam of light.

The optical axis is an imaginary line that defines the center of the path along which light propagates. The string shape is accordingly determined perpendicularly to the center of the path along which the light propagates. From this it should be understood that the string shaped beam of light is a shape of an illuminated field in a plane perpendicular to the optical axis. Accordingly the length and the width of the string shaped beam of light as well as its distance to the grasping space may differ from one plane perpendicular to the optical axis to another plane perpendicular to the optical axis. Generally, and preferably the length and the width of the string shaped beam of light increase from one plane perpendicular to the optical axis and closer to the projector to a plane perpendicular to the optical axis and further from the projector.

At least the projector of the light emitting arrangement is at least temporally fixed to the surgical instrument proximally to the jaws i.e. on the side of the jaws towards the handle. The projector is arranged to project the string shaped beam of light such that it will be broken upon a lateral movement of an object into the grasping space.

A lateral movement is a movement which is substantially sideways relative to the optical axis of the string shaped beam of light and preferably a movement in a plane perpendicular to the optical axis.

Due to the light emitting arrangement the surgical instrument assembly of the invention is much simpler and more safe to handle than prior art surgical instruments e.g. as described in the introduction. The maneuverability is improved to ensure a correct position prior to grasping thereby reducing any risk of unintended tissue damage and/or reduced risk of slipping or dropping the needle during suturing. In addition, it will be possible to minimize the duration of a surgical procedure as maneuvering will be more accurate.

The surgical instrument assembly may be applied in any type of minimally invasive surgery. The shape and the size of the surgical instrument and its grasper are adapted to the specific type of minimally invasive surgery procedure to be performed such as it is generally known in the art with the difference that the surgical instrument is modified to be a surgical instrument assembly of an embodiment of the present invention.

The terms "distal" and "proximal" should be interpreted in relation to the orientation of the surgical tool i.e. the distal end of the surgical instrument is the part of the surgical tool furthest from the handle portion which constitutes the proximal end of the surgical instrument.

The phrase "proximal" or "proximally to the jaws" (or another object) means closer to the handle portion than the jaws (or the mentioned element).

The term "substantially" should herein be taken to mean that ordinary product variances and tolerances are comprised.

The term "about" is generally used to include what is within measurement uncertainties. When used in ranges the term "about" should herein be taken to mean that what is within measurement uncertainties is included in the range.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

Throughout the description or claims, the singular encompasses the plural unless otherwise specified or required by the context. In particular the singular expression of "string shaped beam of light" also should be interpreted to encompass the plural version "string shaped beams of light" unless it is clear from the context that only the singular version is included.

The handle portion may comprise a handle for being operated by a human surgeon or a connector for being connected to or integrated with a robot for robotic operation.

Unless otherwise specified or clear from the context the term "surgeon" is should be interpreted to an operator of the surgical instrument, wherein the operator may be a human operator (human surgeon) or a robotic operator i.e. a robot programmed to handle the surgical instrument.

The projector may be temporally fixed or permanently fixed e.g. as described for the projector in WO 15/124159 with the modification that the projector of the surgical instrument assembly is mounted to the surgical instrument to project a string shaped beam of light as described above. Further examples are disclosed below.

In an embodiment the grasper has a grasper axis defined as the center axis of the jaws in a closed grasper position. The projector is arranged to project the string shaped beam of light such that it will be broken upon a lateral movement substantially perpendicular to the center axis of the jaws of an object into the grasping space.

In an embodiment the grasper axis is defined as the straight line between a shaft connected to the jaws and the most distal apex of the grasper in a closed position.

The optical axis of the projected beam of light is preferably about parallel with the grasper axis or with an angle of up to about 30 degrees, preferably up to about 20 degrees, such as up to 10. The optimal angle depends on the shape and size of the grasper jaws. In an embodiment the angle of the projected beam of light is adjustable by the user. Thereby the user may optimize the angle during use. Also some surgeons prefer a than other e.g. depending on their experience in performing minimally invasive surgery procedures.

In an embodiment the projector is arranged to project the string shaped beam of light such that it will be broken upon a lateral movement substantially perpendicular to the center axis of the jaws and in a propagation plane comprising at least one of said jaws in open and/or in closed grasper position of an object into the grasping space, where the propagation plane is determined perpendicular to the optical axis.

In an embodiment the lateral movement of the object into the grasping space, which breaks the light beam is advantageously from a lateral distance to the grasping space which is up to about the length of the shortest movable jaw, such a up to about half the length of the shortest movable jaw. In this connection it should be understood that at least one of the jaws is movable and depending on the design of the grasper of the surgical instrument two or more jaws may be movable. The shortest of the movable jaws is very decisive for the operation of the surgical instrument and in particular for the risk of performing unintended tissue damage due to a relatively small body cavity for the minimally invasive surgery and poor vision of the surgical target area and a resulting poor positioning of the jaws prior to closing the jaws to the closed grasper position.

In an embodiment the lateral movement of the object into the grasping space is advantageously from a lateral distance to the grasping space which is up to about 3 times the maximal distance between the distal jaw apexes in the open position of the grasper, such as up to about 2 times, such as up to about the maximal distance between the distal jaw apexes in the open position of the grasper.

In an embodiment the lateral movement of the object into the grasping space is advantageously from a lateral distance to the grasping space which is up to about 50%, such as up to about 30% of the maximal distance between the distal jaw apexes in the open position of the grasper.

As mentioned the surgical instrument and its grasper may have different sizes and design in dependence of its intended use.

In an embodiment the lateral movement of the object into the grasping space is advantageously from a lateral distance to the grasping space which is up to about 5 cm, such as up to about 2 cm, such as up to about 1 cm, such as up to about 5 mm, such as up to about 2 mm, such as up to about 1 mm.

In an embodiment the projector is arranged to project the string shaped beam of light such that the string shaped beam of light has a minimum distance to the jaws in closed grasper position which is up to about 3 times the length of the shortest movable jaw, such a up to about 2 times, such as up to about 100% of, such as up to about half the length of the shortest movable jaw.

The length of the shortest movable jaw is determined from the jaw root such as a hinge, of the movement, such as the tilting movement, to the distal apex of the jaw.

In general it is desired that the minimum distance of the string shaped beam of light to the jaws in closed grasper position is rather short, however, preferably not so short or arranged such that the jaws will break the string shaped beam of light upon being moved to the open grasper position.

In an embodiment the string shaped beam of light is shaped and projected such that the string shaped beam of light is not broken by one or more of the jaws upon being moved to the open grasper position.

In an embodiment each of the jaws has a distal apex and the projector is arranged to project the string shaped beam of light such that the string shaped beam of light has a minimum distance to the jaws in closed grasper position which is up to about 3 times the maximal distance between the distal jaw apexes in the open position of the grasper, such as up to about 2 times, such as up to about 100% of, such as up to about 50% of, such as up to about 30% of the maximal distance between the distal jaw apexes in the open position of the grasper.

In an embodiment the projector is arranged to project the string shaped beam of light such that the string shaped beam of light has a minimum distance to the jaws in closed grasper position which is up to about t about 5 cm, such as up to about 2 cm, such as up to about 1 cm, such as up to about 5 mm, such as up to about 2 mm, such as up to about 1 mm.

The string shaped beam of light may in principle have any string shape determined perpendicularly to the optical axis of the beam of light.

In an embodiment the string shaped beam of light is substantially straight. In this embodiment the projector or projectors are advantageously arranged to project two or more string shaped beams of light e.g. arranged on opposite sides of the grasper e.g. arranged substantially parallel to straight line(s) between jaw apexes.

In an embodiment the string shaped beam of light is angled or curved.

The angled string shaped beam of light may have any number of angles, such as 1, 2, 3 or more. The angled string shaped beam of light may e.g. be a rectangular or square string shaped beam of light extending around the grasper.

The curved string shaped beam of light may be fully curved—i.e. curved in its entire length e.g. in half ring shape or a full ring shape surrounding the grasper, or the string shaped beam of light may be partially curved e.g. comprising a curved section and a straight section.

In an embodiment the string shaped beam of light has a length determined in a propagation plane perpendicular to the optical axis of the beam of light, which length is gradually increasing from a propagation plane closer to the projector to a propagation plane further from the projector.

The area distal to the grasping space, in the following called the distal grasping space, will advantageously also be partly or fully encircling the string shaped beam or beams of light which have propagated to a propagation plane beyond the grasper. In an embodiment the projector is arranged to project the string shaped beam of light such that it will be broken upon a lateral movement of an object into the distal grasping space.

In an embodiment the length of the string shaped beam of light perpendicular to the optical axis or optionally the length of two or more string shaped beams of light together, preferably is at least about 50%, such as preferably at least about 100%, such as at least about 110% of the maximal distance between the distal jaw apexes in the open position of the grasper at a jaw apex propagation plane perpendicular to the optical axis and comprising at least one of the jaw apexes preferably in the open grasper position and/or comprising at least the in closed grasper position most distal apex. Thereby the extension of the string shaped beam(s) of light in its length direction of the string shaped beam of light fully covers any gate into the grasping space such that any lateral movement into the grasper space will result in that the string shaped beam of light is broken.

In an embodiment the length of the string shaped beam of light at the jaw apex propagation plane extends from in the vicinity of one of the jaws to in the vicinity to another one of the jaws, preferably the string shaped beam of light at the jaw apex propagation plane is substantially straight and substantially parallel to a line between the one and the another of the jaws in the jaw apex propagation plane.

The phrase "in the vicinity of" means in an embodiment with a distance up to about the minimum distances given above between the string shaped beam of light and the jaws in open and/or closed grasper position given above.

In an embodiment the string shaped beam of light is part of a light pattern, such as a light pattern comprising spatially dispersed light beam fractions, an angular light path surrounding a light dot or a grid of lines, e.g. a crosshatched pattern optionally comprising substantially parallel lines when emitted to a planar surface, and/or one or more angular, such as rectangular shapes e.g. square shaped, e.g. in an overlapping configuration, in a side by side configuration or concentrically arranged.

In an embodiment the string shaped beam of light is part of a light pattern comprising, a plurality of angled lines and/or a coded structured light configuration.

The light pattern may for example be as described in WO 15/124159 and/or in DK PA 2015 70483 with the modification that the light pattern comprises a string shaped beam of light projected such that it will be broken upon a lateral movement of an object into the grasping space.

The grasper may comprise any number of jaws. Most graspers comprise two jaws, but in some applications it is desired that the grasper has 3 or 4 or even more jaws.

In an embodiment the grasper comprises 2 jaws where one (single-action) or both (double-action) are movable. The movability of the jaw or jaws is advantageous in a tilting movement of the jaw extending from a jaw root to the distal apex of the jaw.

In an embodiment where the grasper has two jaws the light emitting arrangement comprises two or more projectors wherein the pattern light source is operatively connected to the projectors for projecting two or more string shaped beam of lights, preferably comprising one string shaped beam of light on either side of a plane comprising a movement orientation of one or both of the jaws.

In an embodiment the grasper comprises 3 or more jaws and the one or more string shaped beam or beams of light are adapted to the jaws arrangement to ensure that the string shaped beam of light will be broken upon a lateral movement of an object into the grasping space.

The present invention is in particular beneficial where the surgical instrument is a needle holder because the maneuvering of a needle holder often requires using two surgical instruments and comprises passing the suture needle between the needle holders several times and comprises grasping of both needle and thread several times in the surgical operating space. A needle holder is sometimes also referred to as a needle driver.

In an embodiment the surgical instrument is a needle holder and the needle holder comprises two jaws, preferably at least one of the jaws is a hinged jaw.

The needle holder advantageously comprises a ratcheted locking and release mechanism for firmly securing and releasing a suture needle. The locking and release mechanism is advantageously controlled via a control mechanism in the handle portion. An important consideration is that the release mechanism is easy to operate, as the surgeon must grasp and release the needle repeatedly whilst suturing. The position of the release mechanism on the handle portion and the number of teeth on the ratchet are both factors in determining ease of use. In an embodiment the locking and release mechanism also includes a spring that can be adjusted to enable precise tensioning of the jaws on a variety of needle diameters. Advantageously the surgical instrument and the locking and release mechanism are operated by means of a spring-loaded palm grip on the handle portion. Optionally the grip is squeezed to close the jaws and released to open them or visa verse.

The grasper may have double-action or single-action jaws, with the latter being the more common. The jaws are advantageously tapered towards their apex to offer improved visibility at the suture site. The inner surface of the jaws may be coated with diamond or profiled with cross-serrated ribbing for a secure grip. The edges of the jaws are advantageously rounded to prevent damage to the suture material. The needle holder may include an integral knot pusher, e.g. comprising a notch at or near one of the jaw apexes, which can be used to drive an externally tied knot into the body cavity during suturing. In an embodiment the needle holder comprises a suture cutting blade e.g. located close to jaw roots which may be a hinged jaw joint such that it is protected during normal usage.

In an embodiment the surgical instrument is a stapler, a pair of scissors or forceps, such as a biopsy forceps. The surgical instrument in the form of a needle holder, a stapler, a pair of scissors or forceps may be as the corresponding prior art surgical instruments with the modification that it is combined with a light emitting arrangement to form a surgical instrument assembly as described above.

Advantageously the surgical instrument comprises a shaft portion proximally to the jaws of the grasper, the projector of the light emitting arrangement is preferably mounted at the shaft, and preferably the shaft connects the handle portion to the grasper.

In an embodiment the projector of the light emitting arrangement is at least temporally fixed to the surgical instrument at a distance to the jaws which is up to about the length of the shortest of the jaw determined from jaw jaw root, such a jaw hinge, to the distal apex of the jaw, such as up to half of the length of the shortest of the jaws, such as up to 25% of the length of the shortest of the jaws. Preferably the projector of the light emitting arrangement is at least temporally fixed to the surgical instrument immediately adjacent and proximally to the jaws.

By arranging the projector close to the jaws and preferably to project one or more string shaped beams of light such that it will not be broken by the jaws in the open grasper position, a very good confinement of the grasping space may be obtained. The phrase "confinement of the grasping space" means that any lateral movement of an object into the grasping space will break the string shaped beam of light.

In an embodiment the projector of the light emitting arrangement is at least temporally fixed in a rigid connection to the surgical instrument such that the light projection is not unintentionally changed.

In an embodiment the light emitting arrangement comprises two or more light sources.

In an embodiment the light emitting arrangement is detachable from the surgical instrument, preferably at least the projector of the light emitting arrangement is configured for being temporarily fixed to the surgical instrument by a click lock, a sleeve lock, a screw lock, a turn lock, a wedge lock or combinations thereof.

In an embodiment the projector of the light emitting arrangement is incorporated in or mounted to a sleeve, preferably comprising a sleeve end edge portion comprising the projector, the sleeve being configured for being mounted onto the surgical instrument.

In an embodiment at least the projector of the light emitting arrangement is permanently fixed to the surgical instrument.

The light source may be any kind of light source such as the light sources described in WO 15/124159 and/or in DK PA 2015 70483.

The light emitting arrangement is advantageously configured for emitting light at a power in the interval of from about 1 mW to about 1 W and preferably the power is selectable for a user.

Advantageously the wavelength(s) of the light emitting arrangement of the surgical instrument assembly is tunable for example in a coordinated way relative to movements in a distal-proximal direction of the surgical instrument inserted through an access port of a cannula e.g. as described in DK PA 2015 70483 where the relative movements between the surgical instrument and the cannula are tuning the wavelengths.

The projector may for example be as described in WO 15/124159 and/or in DK PA 2015 70483 with the modification that the projector is arranged to project the string shaped beam of light such that it will be broken upon a lateral movement of an object into the grasping space.

The light source may advantageously be optically connected to the projector to transfer light to the projector via an optical fiber which is advantageously protected by a polymer cover.

The light source may be incorporated in the handle portion or alternatively arranged at a distance to the surgical instrument e.g. by being incorporated into a light source housing arranged to be positioned at a distance to the surgical instrument. The light source is powered by a battery or by the electrical network.

In an embodiment the surgical instrument assembly comprises a cleaning element for cleaning the projector, the cleaning element is preferably in the form of a wiping element arranged for wiping and/or washing the projector or a spray element arranged for spraying or blowing the projector with a fluid such as gas and/or liquid. Such cleaning element may advantageously be as described in DK PA 2015 70483.

The invention also comprises a sleeve assembly suitable for forming part of a surgical instrument assembly as described above.

The sleeve assembly comprises a sleeve and a light emitting arrangement, where the light emitting arrangement advantageously is as described above and the sleeve is configured for mounting at least the projector to a surgical instrument. The projector is configured for being at least temporarily and rigidly fixed to the sleeve. Advantageously the sleeve comprises a sleeve end edge portion comprising the projector.

The sleeve arrangement may be as the sleeve arrangement described in WO 15/124159, with the difference that the projector is configured for projecting a string shaped beam of light as described above.

In an embodiment the sleeve is configured to cover at least a shaft portion of the surgical instrument such that the projector is arranged to project the string shaped beam of light such that it will be broken upon a lateral movement of an object into the grasping space of the surgical instrument.

The invention also comprises a robot for performing minimally invasive surgery.

The robot is configured for operating at least one surgical instrument assembly as described above. The robot comprises a robot arm for handling the surgical instrument of the surgical instrument assembly and a computer system comprising a robot controller for controlling the robot arm. The robot further comprises a light sensor system in data communication with the computer system and configured for sensing breaches of the string shaped beam and for transmitting sensing data to the computer system, wherein the robot controller is configured for operating the surgical instrument by the robot arm based on operation data comprising the sensing data.

In an embodiment the computer system comprises at least one set of instructions for performing a minimally invasive surgery. The operation data comprises at least a part of the instructions. Preferably the computer system comprises a database comprising a plurality of sets of instructions and a user interface for selecting which set of instructions are to be applied and/or for submitting additional and/or replacement instructions to the robot.

In an embodiment the surgical instrument assembly is integrated with the robot and the surgical instrument is permanently fixed to the robot arm.

Advantageously the computer system is further configured for receiving depiction data comprising
  three-dimensional (3D) data representing at least one surface section in 3D space of a minimally invasive surgery cavity, wherein the surface section comprises a target area,
  real time spatial position data of the surgical instrument and for transmitting the obtained spatial position data to the computer system, and
  surface position data of at least the target area,
wherein the operation data comprises at least a part of the depiction data.

The depiction data may e.g. be obtained and submitted to the computer as described in DK PA 2015 70642.

In an embodiment the surgical instrument is a needle holder and the minimally invasive surgery comprises performing a suturing.

The invention also comprises a method of performing minimally invasive surgery of a target surgical area in a body cavity below a skin area of a patient.

The method comprises providing access to the surgical target area comprising providing at least one incision through the skin area and inserting
  an illumination element for illuminating the target area,
  a light sensor system comprising a camera for acquiring images of the target area, and
  at least one surgical instrument assembly as described above,
wherein the light sensor system is configured for sensing breaches of the string shaped beam and for transmitting sensing data to a computer system for being displayed on a monitor and/or for forming part of operation data for operating the surgical instrument by a robot arm, such as the robot arm of the robot described above.

In an embodiment the surgical instrument is a needle holder and the minimally invasive surgery comprises performing a suturing of a wound. The method comprises
  inserting a second surgical instrument comprising a grasper,
  providing a suture needle with needle front having an apex and a needle rear carrying a suture thread,
  grasping the suture needle with the needle holder,
  driving the apex of the needle through tissue adjacent to the wound and providing that the apex exit the tissue,
  grapping the needle front with the second surgical instrument and pulling out the needle to form a stitch and
  securing the stitch by forming a knot and/or by welding sections of the suture.

A suture thread is in the prior art also referred to as a suture tail.

Preferably the second surgical instrument is part of a surgical instrument assembly as described above.

In an embodiment the method comprises manipulating the needle between the needle holder and the second surgical instrument, optionally the second surgical instrument is a pair of forceps or a second needle holder.

All features of the invention and embodiments of the invention as described above including ranges and preferred ranges can be combined in various ways within the scope of the invention, unless there are specific reasons not to combine such features.

BRIEF DESCRIPTION OF THE DRAWINGS

The above and/or additional objects, features and advantages of the present invention will be further elucidated by the following illustrative and non-limiting description of embodiments of the present invention, with reference to the appended drawings.

FIG. 13 is a schematic topside view of an embodiment of a surgical instrument assembly of the invention with two projectors.

FIGS. 13a and 13b are sectional views seen in respectively the A-A cut and the B-B cut.

The figures are schematic and simplified for clarity. Throughout, the same reference numerals are used for identical or corresponding parts.

Further scope of applicability of the present invention will become apparent from the description given hereinafter. However, it should be understood that the description and specific examples, while indicating preferred embodiments of the invention, are given by way of illustration only, since various changes and modifications within the spirit and scope of the invention will become apparent to those skilled in the art from this description and examples.

Figure 1:
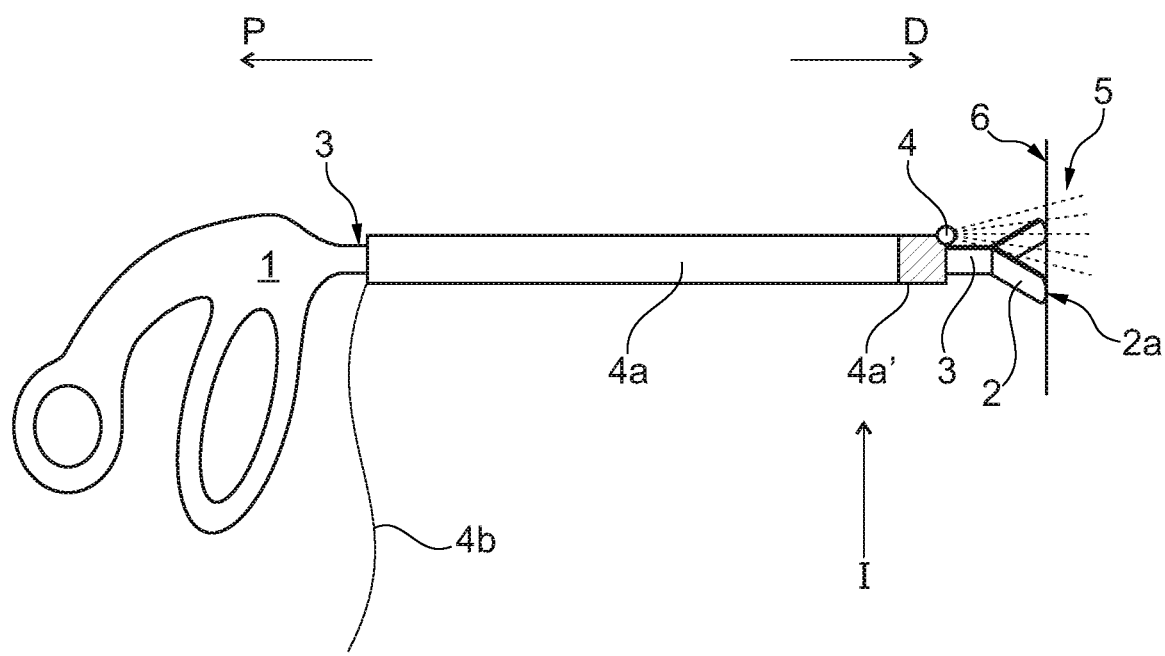
FIG. 1 is a schematic side view of an embodiment of a surgical instrument assembly of the invention showing the handle portion at its proximal end and the grasper at its distal end.

The surgical instrument assembly shown in FIG. 1 comprises a light emitting arrangement and a surgical instrument, the surgical instrument has a distal end D and a proximal end P and comprises a handle portion 1 at its proximal end and a grasper 2 at its distal end. The shown grasper comprises two jaws, but it should be understood that the grasper may have further jaws as explained above. Each of the jaws of the grasper 2 has an apex 2a. The handle portion 1 is connected to the grasper 2 by a shaft 3. Such a shaft is sometimes referred to as a body portion.

The light emitting arrangement comprises a not shown light source for generating light and a projector 4 for projecting a beam of light 5 comprising a string shape perpendicular to the optical axis of the beam of light. The projector 4 is temporally fixed to the surgical instrument via a sleeve 4a comprising a fixing sleeve 4'a. Advantageously the projector 4 is fixed to the sleeve 4'a mechanically e.g. by a locker or a clamp. The not shown light source is in optical connection with the projector 4 by an optical fiber 4b.

The projector 4 is fixed proximally to the jaws of the grasper 2 and is arranged to project the string shaped beam of light 5 such that it will be broken upon a lateral movement of an object into the grasping space between the jaws of the grasper 2. As indicated with the plane 6 perpendicular to the optical axis of the beam of light and comprising the apexes 2a, the string shaped beam of light 5 has a length corresponding to the distance between the jaws in their open position, thereby ensure that the string shaped beam of light 5 will be broken upon a lateral movement of an object from the shown side of the grasper 2 and into the grasping space.

The expression that a plane comprising the apex, means that the apex is a that plane.

Figure 2:
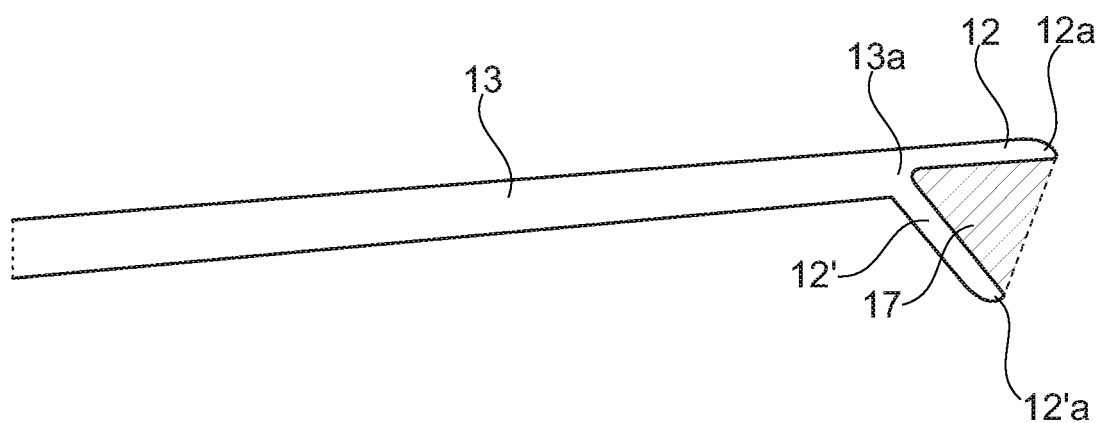
FIG. 2 is a schematic side view of an embodiment of a surgical instrument assembly of the invention where only a part of the shaft and the grasper is shown and the grasper has single-action jaws.

The surgical instrument assembly shown in FIG. 2 comprises a grasper rigidly connected to a shaft 13. The grasper comprises two jaws 12, 12' with respective apexes 12a, 12'a. The grasper has single-action jaws 12, 12' which means that only one of the jaws 12' is movable in a tilting movement from a hinge 13a. The grasping space 17 i.e. the space in which an object will be grasped upon closing of the jaws 12, 12', is indicated by hatching.

Figure 3:
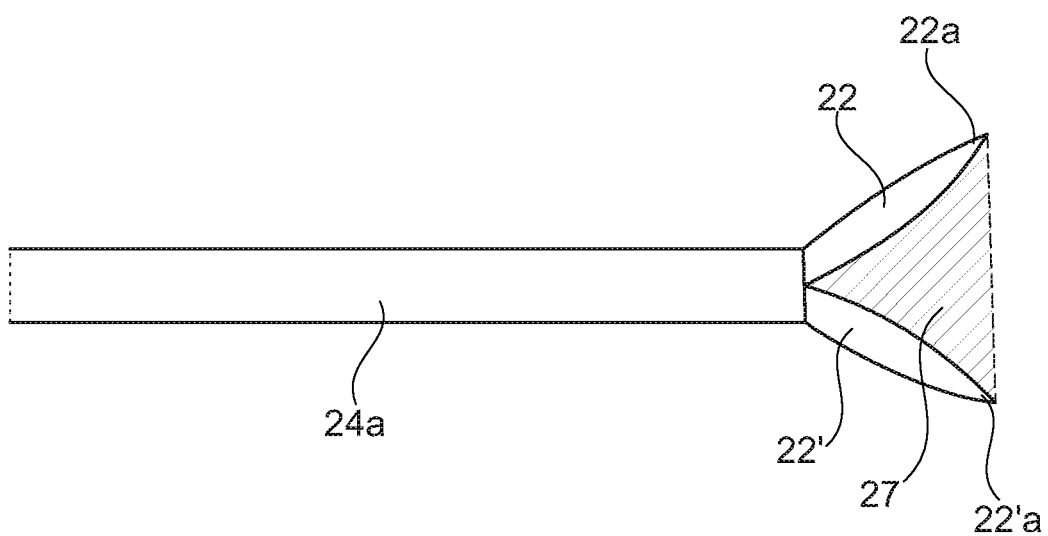
FIG. 3 is a schematic side view of an embodiment of a surgical instrument assembly of the invention where only a part of the shaft and the grasper is shown and the grasper has double-action jaws.

The surgical instrument assembly shown in FIG. 3 comprises a grasper rigidly connected to a not shown shaft covered by a sleeve 24a carrying a not shown projector. The grasper comprises two jaws 22, 22' with respective apexes 22a, 22'a. The grasper has double-action jaws 22, 22' which means that both of the jaws 22, 22' are movable in a tilting movement from a not shown hinge. The grasping space 27 i.e. the space in which an object will be grasped upon closing of the jaws 22, 22', is indicated by hatching.

Figure 4:
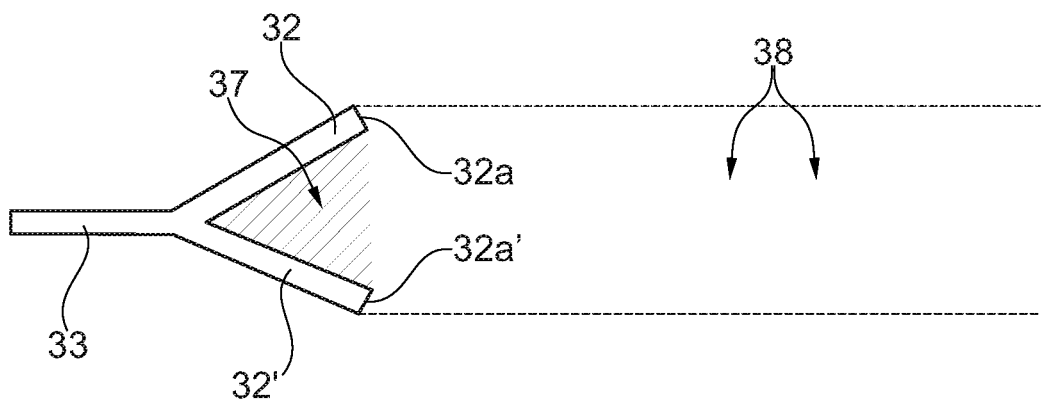
FIG. 4 is a schematic side view of an embodiment of a surgical instrument assembly of the invention where a distal gripping space is indicated.

The surgical instrument assembly shown in FIG. 4 comprises a grasper rigidly connected to a shaft 33. The grasper comprises two jaws 32, 32' with respective apexes 32a, 32'a. The grasper has double-action jaws 32, 32' and is shown in an open position where the grasping space 37 is indicated by hatching. A distal gripping space 38 is indicated with dotted lines to indicate an area distal to the grasping space 37. As the string shaped beam of light propagates further in a distal direction after having passed the apexes 32a, 32'a, the string shaped beam of light will be broken upon a lateral movement of an object into the distal grasping space 38 at a plane perpendicular to the optical axis and distal to the apexes 32a, 32'a.

Figure 5:
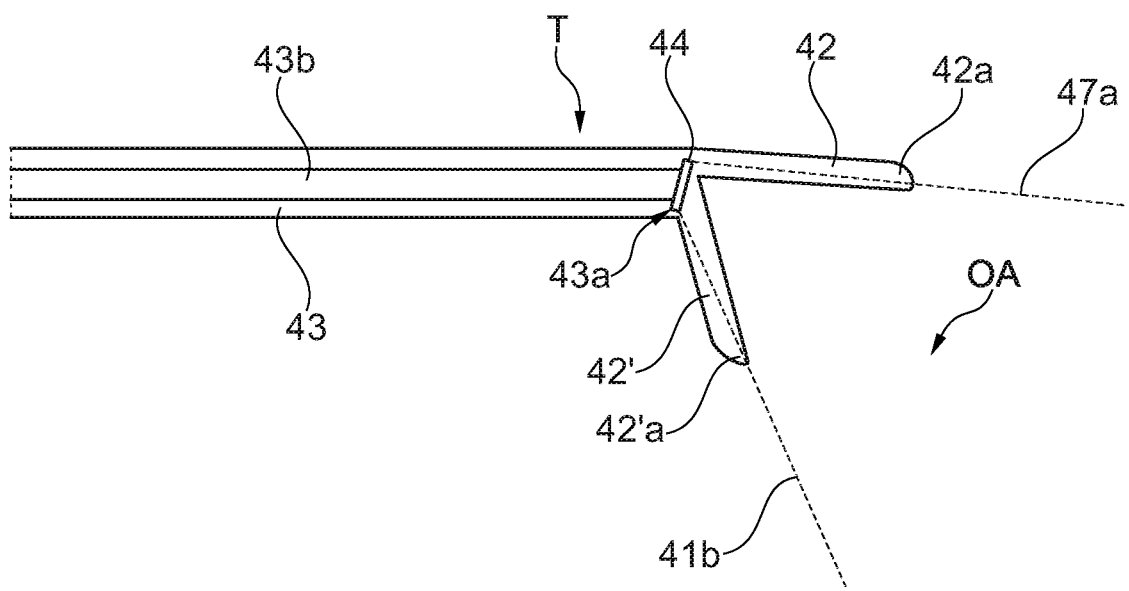
FIG. 5 is a schematic side view of an embodiment of a surgical instrument assembly of the invention where the projector is angled relatively to the shaft.

The surgical instrument assembly shown in FIG. 5 comprises a grasper rigidly connected to a shaft 43. The grasper comprises two jaws 42, 42' with respective apexes 42a, 42'a. The grasper has single-action jaws 42, 42' which means that only one of the jaws 42' is movable in a tilting movement from a hinge 43a. A projector 44 is fixed to the shaft 43 immediately adjacent to the hinge 43a. An optical fiber cable 43b guides the light from a not shown light generator to the projector 44. The projector 44 is angled relatively to the shaft 43 to emit the string shaped beam of light 47a, 47b, such that is has an optical axis OA which is angled relatively to the shaft 43.

The string shaped beam of light 47a, 47b has a length extending from the line 47a to the line 47b and as seen the length of the string shaped beam of light 47a, 47b increases as the string shaped beam of light propagates along its optical axis OA. In the plane perpendicular to the optical axis and comprising the apexes 42a, 42'a when the grasper is in its open position, the string shaped beam of light 47a, 47b has a length which is substantially identical to the distance between the apexes 42a, 42'a. The light projected from the projector 44 thereby forms a string shaped beam of light 47a, 47b that spreads out as a fan as the light propagates.

Figure 6:
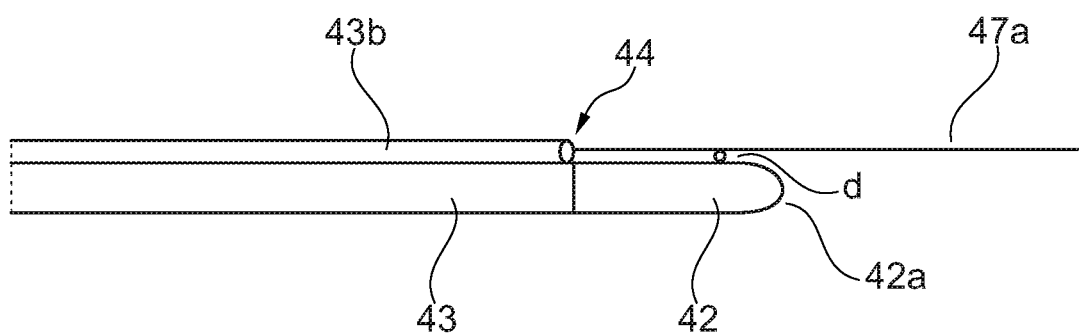
FIG. 6 is a schematic view of the surgical instrument assembly of FIG. 5 seen in the topside view as indicated in FIG. 5.

In FIG. 6 the surgical instrument assembly of FIG. 5 is seen in the topside view as indicated with "T" in FIG. 5. As it can be seen the distance between the string shaped beam of light and jaw apex 42a is very narrow. The minimum distance d between the beam of light is also narrow. Further the minimum distance d between the string shaped beam of light and the jaw 42 is substantially constant along the length of the jaw 42 except for at the apex where it is slightly larger.

Figure 7:
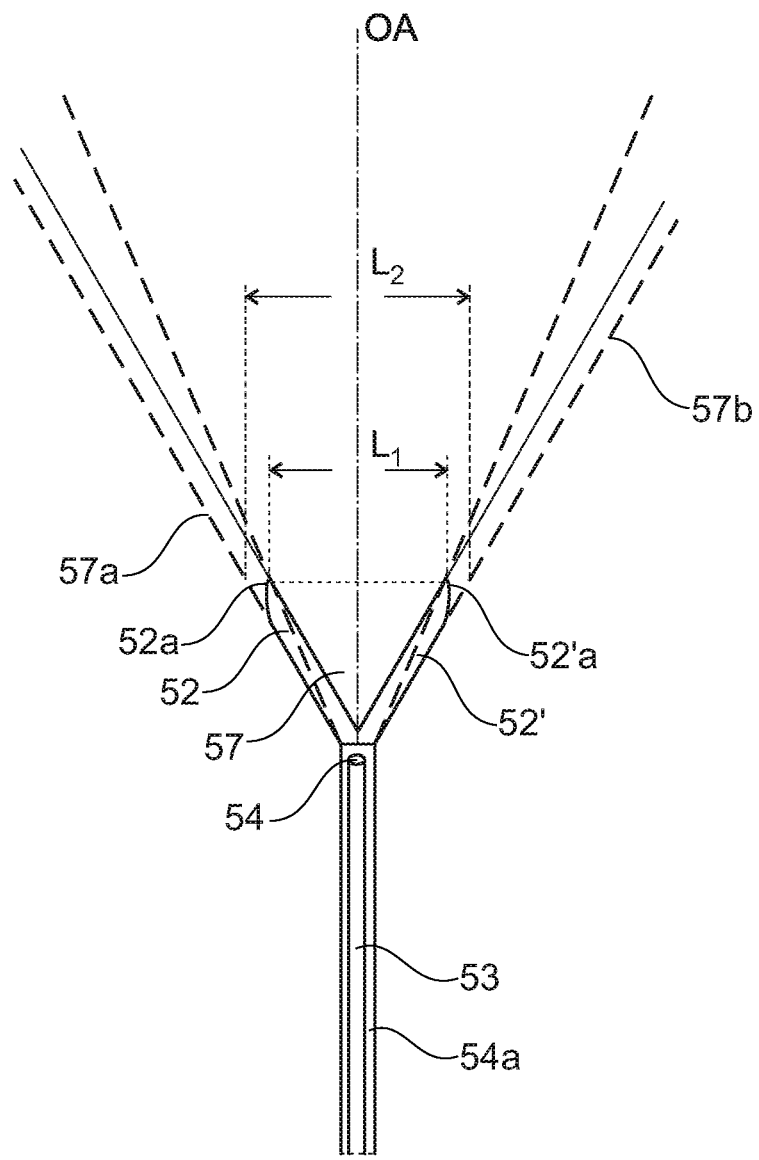
FIG. 7 is a schematic side view of an embodiment of a surgical instrument assembly of the invention where the propagation of the string shaped beam of light is indicated.

The surgical instrument assembly shown in FIG. 7 comprises a grasper rigidly connected to a shaft 53. The shaft 53 is fully covered by a sleeve 54 (which is shown as a transparent sleeve 54*a*) with a fixed projector 54. The grasper comprises two jaws 52, 52' with respective apexes 52*a*, 52'*a*. The grasper has double-action jaws 52, 52' and both of the jaws 52, 52' are movable in a tilting movement from a not shown hinge.

The projector 54 is straight relative to the shaft 53 to emit the string shaped beam of light 57*a*, 57*b*, such that is has an optical axis OA which is parallel with the shaft 53.

The string shaped beam of light 57*a*, 57*b* has a length extending from one of the selectable lines 57*a* to one of the selectable lines 57*b*. The lines 57*a*, 57 indicate the width of the fan of light as it spreads out as the string shaped beam of light propagates. The length of the string shaped beam of light 57*a*, 57*b* increases as the string shaped beam of light propagates along its optical axis OA. The selectable lines 57*a* and 57*b* are selected by a user by selecting the length of the string shaped beam of light in a plane perpendicular to the optical axis such as in the plane perpendicular to the optical axis and comprising the apexes 52*a*, 52'*a*. As indicated the string shaped beam of light may be selected to have the length L1 or the length L2 at the plane perpendicular to the optical axis and comprising the apexes 52*a*, 52'*a*.

Figure 8:
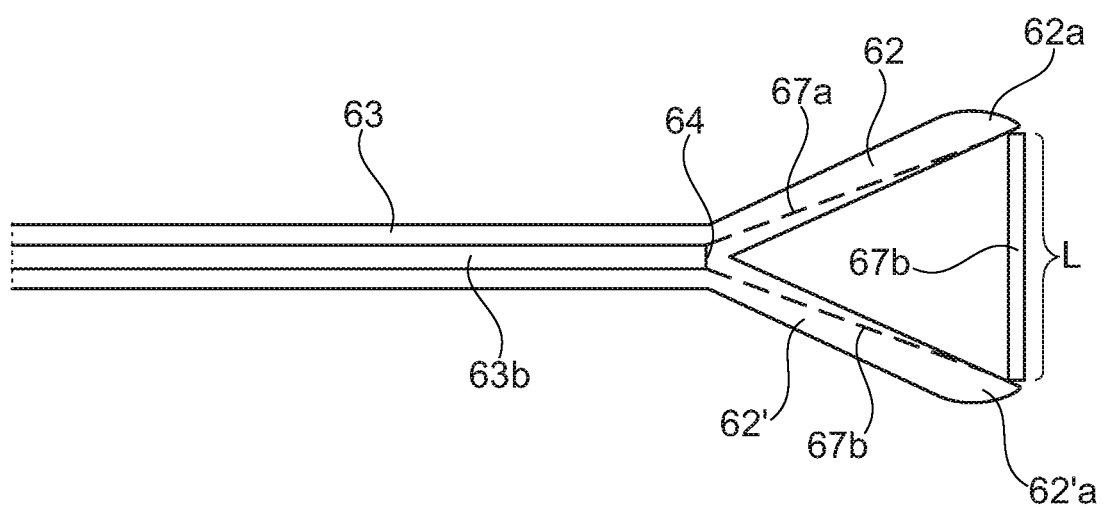
FIG. 8 is a schematic side view of an embodiment of a surgical instrument assembly of the invention where the length of the string shaped beam of light at the jaw apexes is indicated.

The surgical instrument assembly shown in FIG. 8 comprises a grasper rigidly connected to a shaft 63. The grasper comprises two jaws 62, 62' with respective apexes 62*a*, 62'*a*. A projector 64 is fixed to the shaft 63 and an optical fiber cable 63*b* guides the light from a not shown light generator to the projector 64. The projector 64 emits a string shaped beam of light 67*a*, 67*b* propagating to form a fan of light as it spreads out. At the plane perpendicular to the optical axis and comprising the apexes 62*a*, 62'*a*, the string shaped beam of light is marked with ref. no. 67*s* and it can be seen that it has a length L substantially identical to the distance between the jaws 62, 62*a*. The length of the string shaped beam of light is advantageously selectable by the user.

Figure 10:
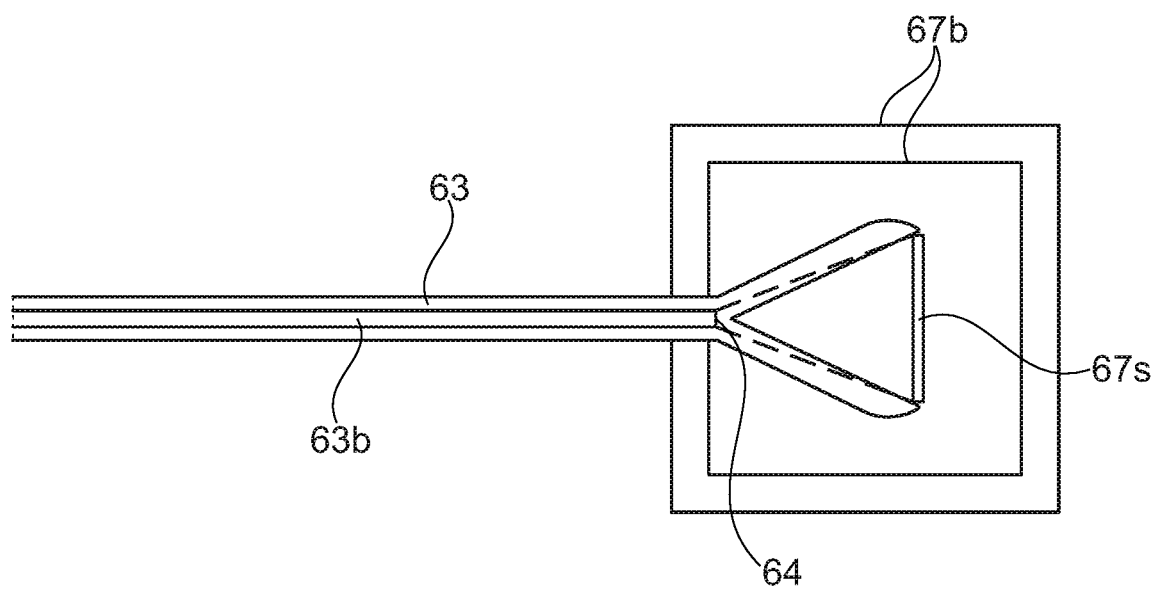
FIG. 10 is a schematic side view of the surgical instrument assembly of FIG. 8, where a light pattern is also projected.

FIG. 10 shows a variation of the surgical instrument assembly of FIG. 8, wherein the projector 64 or another not shown projector simultaneously emits a light pattern 67*p* towards a surgical target area for increasing the visual perception of the 3D space in which the surgical tool is moved and thereby making it simpler for the surgeon to handle the surgical instrument assembly with a high accuracy e.g. as described in WO15124159.

Figure 11:
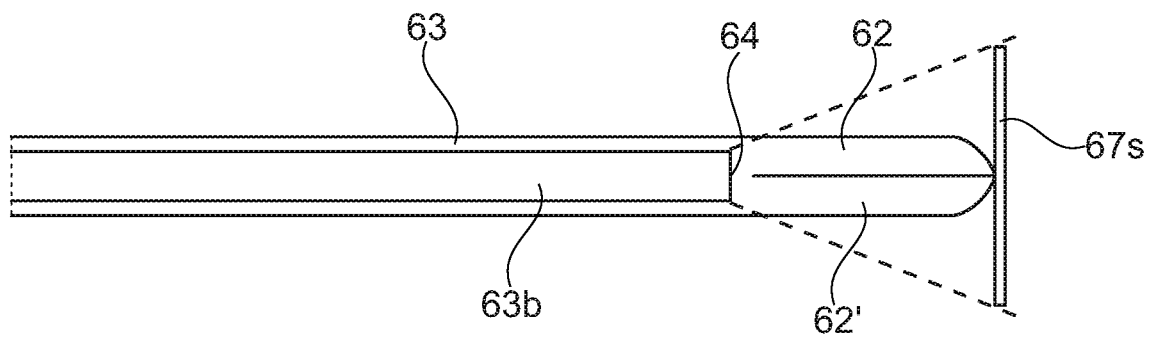
FIG. 11 is a schematic side view of the surgical instrument assembly of FIG. 8, where jaws are in closed grasper position.

FIG. 11 shows the surgical instrument assembly of FIG. 8 in a closed grasper position.

Figure 12:
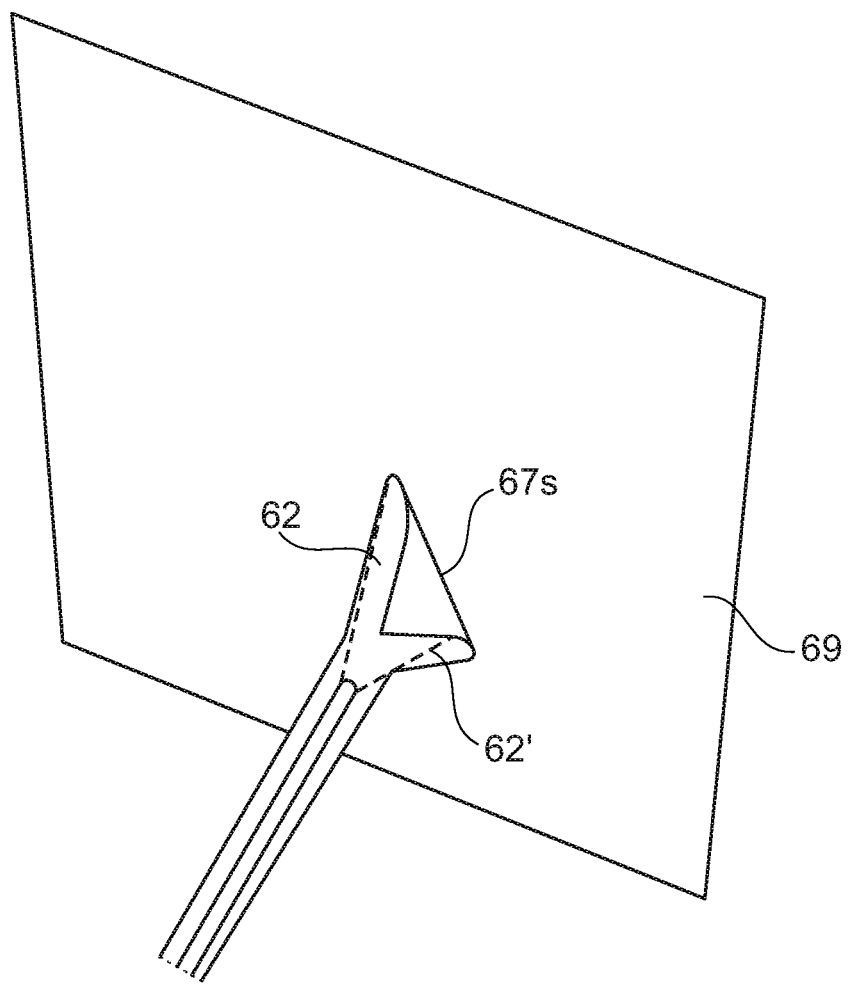
FIG. 12 is a perspective view of the surgical instrument assembly of FIG. 8, where jaws are in open position.

FIG. 12 shows the surgical instrument assembly of FIG. 8 in an open position and in use during surgery where the surgical instrument assembly is moved towards a surgical target area 69 for grapping a not shown protruding object. When the protruding object breaks the string shaped beam of light 67*s* the surgeon will know with a high precision the relative position between the object and the grasping space and the surgeon will thereby be able to position the grasper with a high accuracy before closing the grasper. Thereby erroneous grasping steps and risk of tissue damage connected therewith may be reduced or even avoided.

Figure 9:
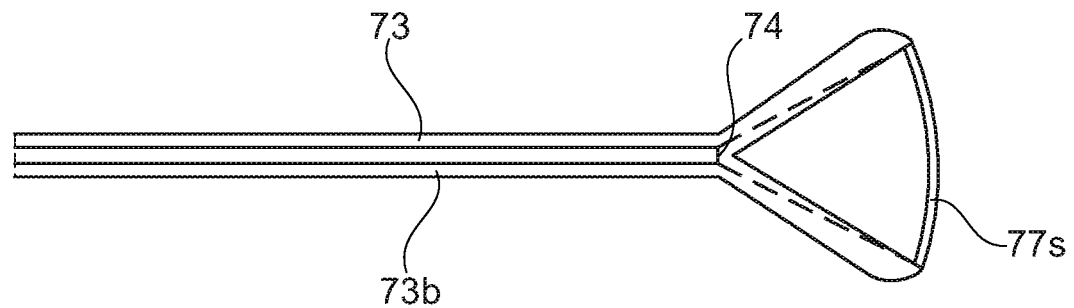
FIG. 9 is a schematic side view of an embodiment of a surgical instrument assembly of the invention where the length and shape of the string shaped beam of light at the jaw apexes is indicated.

The surgical instrument assembly shown in FIG. 9 comprises a grasper rigidly connected to a shaft 73. The grasper comprises two jaws 72, 72' with respective apexes 72*a*, 72'*a*. A projector 74 is fixed to the shaft 73 and an optical fiber cable 73*b* guides the light from a not shown light generator to the projector 74. The projector 74 emits a string shaped beam of light which is curved. This can be seen by the curved string shaped beam of light 77*s* taken in the plane perpendicular to the optical axis and comprising the apexes 72*a*, 72'*a*.

The surgical instrument assembly shown in FIG. 13 comprises a handle portion 81 at its proximal end and a grasper 82 at its distal end. The shown grasper comprises two jaws 82, but only one can be seen. The jaw 82 has an apex 82*a*. Two projectors 84 are fixed to the shaft 83 at a distance from the jaws 82. The projectors each emit a string shaped beam of light 87*a*, 87*b* on either side of the grasper 82. The optical axis of the respective string shaped beam of light 87*a*, 87*b* is angled relatively to the axis of the shaft, such that the distance between the respective string shaped beam of light 87*a*, 87*b* and the jaws 82 increases along the length of the jaws to the maximal distance d at the jaw apex 82*a*. The reference O indicates an object that is about to be moved laterally into the gripping space, and it can be seen that it will break the string shaped beam of light 87*b* when it comes closer to the gripping space, thereby informing a surgeon using the surgical instrument assembly about the relative position of the object to the gripping space. FIG. 13*a* and FIG. 13*b* are sectional views seen in respectively the A-A cut and the B-B cut and show that the string shaped beam of light is longer and wider in a plane perpendicular to the optical axis further from the projector 84 than in a plane perpendicular to the optical axis closer to the projector 84.

Figure 14:
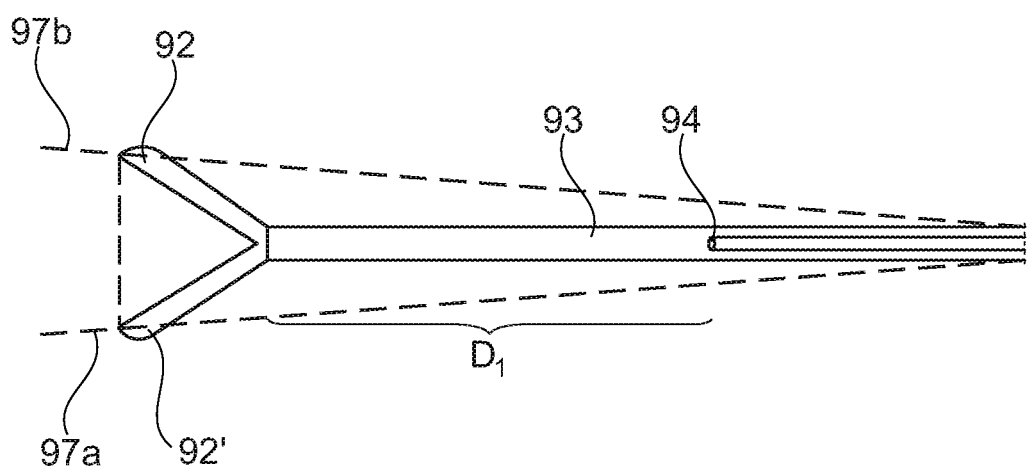
FIG. 14 is a schematic side view of an embodiment of a surgical instrument assembly of the invention where the distance between the projector and the jaws is indicated.

The surgical instrument assembly shown in FIG. 14 comprises a grasper rigidly connected to a shaft 93. The grasper comprises two jaws 92, 92'. A projector 94 is fixed to the shaft 93 at a distance D1 to the grasper. The projector 94 is projecting the string shaped beam of light with length extending from line 97*a* to line 97*b*. As it can be seen the length D1 may be rather large, which for some applications may be beneficial in particular where the body cavity is very narrow.

Figure 15A:
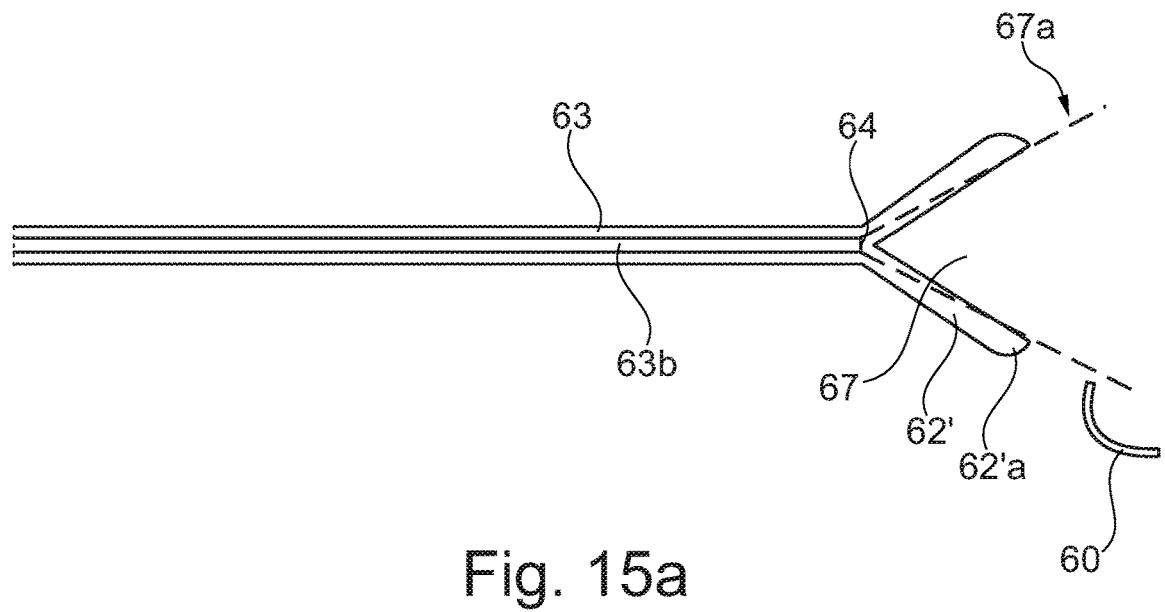
FIGS. 15a and 15b are schematic side views of an embodiment of a surgical instrument assembly of the invention where the surgical instrument assembly is in use.
Figure 15B:
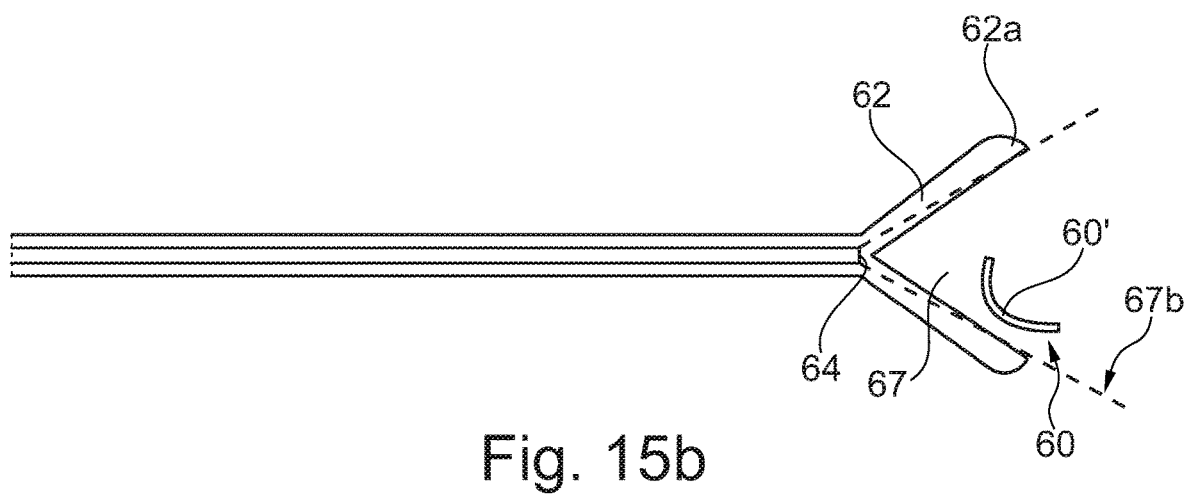

FIGS. 15*a* and 15*b* show the surgical instrument assembly of FIG. 8 in operation during a suturing.

In FIG. 15*a* the grasper is in an open position and a needle 60 is about to be moved towards the grasping space 67 from a certain lateral distance to the grasping space 67 which is larger than the distance between the grasping space 67 and the string shaped beam of light 67*a*, 67*b*. In FIG. 15*b* the needle 60 is moved closer to and is approaching the grasping space 67 and thereby it is breaking the string shaped beam of light 67*a*, 67*b* as indicated with the light marking 60' on the needle 60. At this point the surgeon will know the exact position of the needle relative to the grasping space and he will be able to position the needle 60 in the grasping space 67 with a high accuracy before closing the grasper.

What is claimed is:

1. A surgical instrument assembly for minimally invasive surgery, comprising:
    a surgical instrument having a grasper at a distal end thereof and a handle portion at a proximal end thereof, the grasper having first and second jaws configured to transition between an open position in which a grasping space is formed between the first and second jaws and a closed position, the grasper having a central axis along the first and second jaws in the closed position, each of the first and second jaws having a terminal distal end; and
    a light emitting arrangement having a light source for generating light and a projector for projecting at least a beam of light, the projector being fixed to the surgical instrument proximal to the grasper when the first and second jaws are in the open position, the beam of light having a string shape perpendicular to an optical axis of the beam of light, the projector being offset from the central axis of the grasper;

wherein the projector is arranged to project the beam of light into the grasping space in the open position such that the beam of light is broken upon a lateral movement of an external object into the grasping space, and the beam of light has a maximum length corresponding to a distance between the terminal distal ends of the first and second jaws in the open position.

2. The surgical instrument assembly of claim 1, wherein the projector is removably fixed to an outer surface of the surgical instrument.

3. The surgical instrument assembly of claim 1, wherein one of the first and second jaws is fixed relative to the grasper, and the other of the first and second jaws is configured to move to transition the first and second jaws between the open and closed positions.

4. The surgical instrument assembly of claim 1, wherein the projector is arranged to project the beam of light such that the beam of light has a minimum distance to the jaws in the closed position of about 3 times the length of a shortest jaw of the first and second jaws.

5. The surgical instrument assembly of claim 1, wherein the projector is arranged to project the beam of light such that the beam of light has a minimum distance to the first and second jaws in the closed position of about 5 cm.

6. The surgical instrument assembly of claim 1, wherein the beam of light is curved.

7. The surgical instrument assembly of claim 1, wherein the light emitting arrangement comprises a second projector for projecting a second beam of light having a string shape perpendicular to an optical axis of the second beam of light.

8. The surgical instrument assembly of claim 1, wherein the string shape of the beam of light is part of a light pattern, and the light pattern includes at least one of an angular light path surrounding a light dot, a grid of lines, one or more rectangular shapes in an overlapping configuration, one or more rectangular shapes in a side by side configuration, and one or more rectangular shapes or concentrically arranged.

9. The surgical instrument assembly of claim 1, wherein the projector and the optical axis of the beam of light are angled relative to the central axis of the grasper at a non-zero angle.

10. The surgical instrument assembly of claim 1, wherein the surgical instrument is one of a stapler, a pair of scissors, or a pair of forceps; and the surgical instrument assembly is configured to be incorporated into a surgical robotic system.

11. A surgical instrument assembly for minimally invasive surgery, comprising:

a surgical instrument having a grasper at a distal end thereof, a handle portion at a proximal end thereof, and an elongate shaft extending therebetween and having a longitudinal axis, the grasper having first and second jaws configured to transition between an open position in which a grasping space is formed between the first and second jaws and a closed position; and a light emitting arrangement having a light source for generating light and a projector for projecting at least a beam of light, the beam of light having a string shape perpendicular to an optical axis of the beam of light, and the projector and the optical axis of the beam of light having a non-zero angle relative to the longitudinal axis of the elongate shaft, the beam of light being substantially straight;

wherein the projector is attached to the surgical instrument proximal to the first and second jaws and is arranged to project the beam of light into the grasping space in the open position such that the beam of light is broken upon a lateral movement of an external object into the grasping space.

12. The surgical instrument assembly of claim 11, wherein one of the first and second jaws is fixed relative to the grasper, and the other of the first and second jaws is configured to move to transition the first and second jaws between the open and closed positions.

13. The surgical instrument assembly of claim 11, wherein the light emitting arrangement comprises a second projector for projecting a second beam of light having a string shape perpendicular to an optical axis of the second beam of light.

14. The surgical instrument assembly of claim 11, wherein the beam of light has a maximum length corresponding to a distance between terminal distal ends of the first and second jaws in the open position.

15. The surgical instrument assembly of claim 11, wherein the surgical instrument assembly is configured to be incorporated into a surgical robotic system.

16. A surgical instrument assembly for minimally invasive surgery, comprising:

a surgical instrument having a grasper at a distal end thereof and a handle portion at a proximal end thereof, the grasper having first and second jaws configured to transition between an open position in which a grasping space is formed between the first and second jaws and a closed position, the grasper having a central axis along the first and second jaws in the closed position; and a light emitting arrangement having a light source for generating light and a projector for projecting at least a beam of light, the beam of light having a string shape perpendicular to an optical axis of the beam of light, the projector being offset from the central axis of the grasper;

wherein the projector is arranged to project the beam of light into the grasping space in the open position such that the beam of light is broken upon a lateral movement of an external object into the grasping space, and the projector is arranged to project the beam of light such that the beam of light has a minimum distance to the jaws in the closed position of about 3 times the length of a shortest jaw of the first and second jaws.

17. The surgical instrument assembly of claim 16, wherein the projector is arranged to project the beam of light such that the beam of light has a minimum distance to the first and second jaws in the closed position of about 5 cm.

18. The surgical instrument assembly of claim 16, wherein the beam of light is curved.

* * * * *